United States Patent
Cozzi et al.

[11] Patent Number: 5,362,729
[45] Date of Patent: Nov. 8, 1994

[54] DIHYDROPYRIDINE DERIVATIVES USEFUL IN ANTITUMOR THERAPY

[75] Inventors: Paolo Cozzi; Maria Menichincheri; Laura Capolongo; Nicola Mongelli, all of Milan, Italy

[73] Assignee: Farmitalia Carlo ERBA S.r.l., Milan, Italy

[21] Appl. No.: 937,681

[22] Filed: Sep. 1, 1992

[30] Foreign Application Priority Data

Sep. 19, 1991 [GB] United Kingdom ............. 9119983.6

[51] Int. Cl.$^5$ ............... C07D 401/06; A61K 31/535
[52] U.S. Cl. ................... 514/235.5; 514/339; 514/318; 514/235.8; 546/278; 546/255; 546/256; 546/272; 546/194; 544/121; 544/131; 544/365
[58] Field of Search ............. 546/278, 255, 256, 272, 546/194; 544/121, 131, 365; 514/341, 332, 333, 339, 235.5, 318, 235.8

[56] References Cited

U.S. PATENT DOCUMENTS

| | | |
|---|---|---|
| 3,485,847 | 12/1969 | Bossert et al. |
| 4,044,141 | 8/1977 | Bossert et al. |
| 4,293,700 | 10/1981 | Uldrikis et al. |
| 4,495,356 | 1/1985 | Inoue et al. |
| 4,537,881 | 8/1985 | Heiker et al. |
| 4,690,935 | 9/1987 | Taylor et al. |
| 4,766,213 | 8/1988 | Juraszyk et al. |
| 4,906,646 | 3/1990 | Honn et al. |
| 4,923,871 | 5/1990 | Inaba et al. |
| 4,946,851 | 8/1990 | Semeraro et al. ............... 546/321 |
| 4,948,899 | 8/1990 | Ogawa et al. |
| 4,985,558 | 1/1991 | Suzuki et al. |

FOREIGN PATENT DOCUMENTS

WO90/06923 6/1990 WIPO.

OTHER PUBLICATIONS

Derwent Publications, Abstract No. 90-087298/12 of JP-A-204 0383, Feb. 9, 1990.

Derwent Publications, Abstract No. 84-226628/37 of EP-118120, Sep. 12, 1984.

(List continued on next page.)

Primary Examiner—Jane T. Fan
Attorney, Agent, or Firm—Oblon, Spivak, McClelland, Maier & Neustadt

[57] ABSTRACT

Compounds which are useful in anti-tumors therapy having the formula (I)

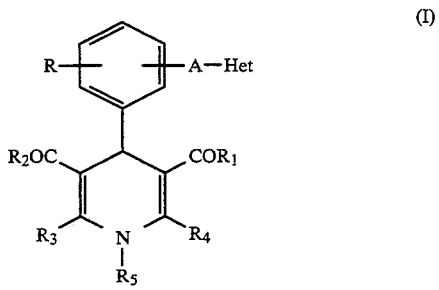

wherein Het imidazole, A represents a direct linkage at the phenyl 4-position: R is hydrogen; one of $R_3$ and $R_4$ is $C_1$-$C_3$ alkyl unsubstituted or omega substituted by $C_1$-$C_3$ alkoxy, and the other, independently, is:

a) $C_1$-$C_3$ alkyl unsubstituted or omega substituted by $C_1$-$C_3$ alkoxy; or b) —$(CH_2)_m$—O—$(CH_2)_n$—$NR_aR_b$ wherein each of m and n, which may be the same or different is an integer of 1 to 3, each of $R_a$ and $R_b$, which may be the same or different, is hydrogen or $C_1$-$C_3$ alkyl; $R_5$ is hydrogen or $C_1$-$C_6$ alkyl unsubstituted or substituted by a morpholino;

each of $R_1$ and $R_2$ is independently a group —OR' wherein R' is $C_1$-$C_6$ alkyl; or a pharmaceutically acceptable salt thereof.

5 Claims, No Drawings

OTHER PUBLICATIONS

Derwent Publications, Abstract No. 86-256850/39 of SU-1 125 957, Mar. 23, 1986.
Derwent Publications, Abstract No. 85-307685/49 of JP-A-0214 786, Oct. 28, 1985.
Derwent Publications, Abstract No. 83-759660/37 of DE-3 207 982, Sep. 8, 1983.
Derwent Publications, Abstract No. 87-322605/46 of EP-245918, Nov. 19, 1987.
Derwent Publications, Abstract No. 87-01278/12 of EP-215250, Mar. 25, 1987.
Derwent Publications, Abstract No. 86-196593/30 of US 4 599 341, Jul. 8, 1986.
Chemical Abstract of DT 2 248 150, Apr. 4, 1974.
Derwent Publications, Ltd., No. 87-0181278, Aug. 19, 1985, & EP-0-215-250, Mar. 25, 1987.
Derwent Publications, Ltd., No: 88-300609, Apr. 9, 1987, & DE-3-711-991, Oct. 20, 1988.
8th Camerino-Noordwijkerhoutsymposium Trends In Receptor Research, Sep. 8-12, 1991, Universit A' Deglstudi di Camerino Aula Magna, pp. 219-220.

DIHYDROPYRIDINE DERIVATIVES USEFUL IN ANTITUMOR THERAPY

The present invention relates to imidazolyl and pyridyl derivatives of phenyl substituted 1,4-dihydropyridines, to a process for their preparation and to pharmaceutical compositions containing them. A first object of the present invention is to provide new compounds of the following formula (I)

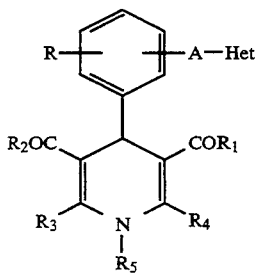

wherein

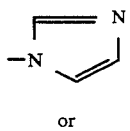

or

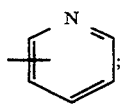

A represents a direct linkage, —CH$_2$—, —CH$_2$—CH$_2$— or, when Het is

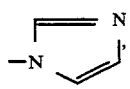

A may also represent —CH=CH—; R is hydrogen, halogen, C$_1$–C$_3$ alkyl or C$_1$–C$_3$ alkoxy; one of R$_3$ and R$_4$ is C$_1$–C$_3$ alkyl unsubstituted or omega substituted by C$_1$–C$_3$ alkoxy, and the other, independently, is a) C$_1$–C$_3$ alkyl unsubstituted or omega substituted by C$_1$–C$_3$ alkoxy; or
b)

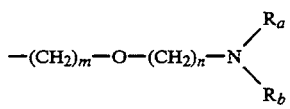

wherein each of m and n, which may be the same or different is an integer of 1 to 3, each of R$_a$ and R$_b$, which may be the same or different, is hydrogen or C$_1$–C$_3$-alkyl or R$_a$ and R$_b$ taken together with the nitrogen atom to which they are linked form a phthalimido group;

R$_5$ is hydrogen or C$_1$–C$_6$ alkyl unsubstituted or substituted by a —N(R$_c$R$_d$) group in which each of R$_c$ and R$_d$ independently is hydrogen or C$_1$–C$_4$ alkyl, or R$_c$ and R$_d$ taken together with the nitrogen atom to which they are linked form a morpholino or piperidino group;

one of R$_1$ and R$_2$ is a group —OR' wherein R' is C$_1$–C$_6$ alkyl either unsubstituted or omega substituted by cyano or C$_1$–C$_3$ alkoxy and the other is, independently, c) C$_1$–C$_3$ alkyl;
d) a group —OR' as defined hereabove; or
e) a group

wherein each of R" and R'" which may be the same or different, is hydrogen or C$_1$–C$_3$ alkyl; or
f) a group —OR$^{IV}$ wherein R$^{IV}$ is hydrogen or a substituent selected from the group consisting of
(i) —(CH$_2$)$_{m'}$—CH=CH—Ph, wherein m' is an integer of 1 to 3 and Ph is a phenyl group either unsubstituted or substituted by one or three substituents chosen among C$_1$–C$_3$ alkyl, C$_1$–C$_3$ alkoxy and halogen;
(ii)

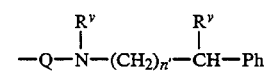

wherein Ph is as defined above; Q is a C$_2$–C$_5$ alkylene radical; n' is zero, 1 or 2; and each R$^v$ is, independently, hydrogen, C$_1$–C$_3$-alkyl or Ph, wherein Ph is as defined above;
(iii)

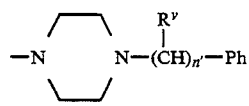

wherein m', n', R$^v$ and Ph are as defined above; and
(iv)

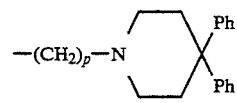

wherein p is 2 or 3 and Ph is as defined above; and the pharmaceutically acceptable salts thereof; and wherein when, at the same time, R$_3$ and R$_4$ are both unsubstituted C$_1$–C$_3$ alkyl, one of R$_1$ and R$_2$ is a group OR' wherein R' is as defined above and the other is as defined above under d), e) or f), then R$_5$ is other than hydrogen.

The invention includes also all the possible isomers and stereoisomers of the compounds of formula (I), and their mixtures. Also the pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I), are included within the scope of the invention, as well as the metabolites thereof.

Pharmaceutically acceptable salts of the compounds of formula (I) are, especially, acid addition salts with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic, fumaric, methanesulfonic and salicylic acids.

Also the salts of the compounds of formula (I) with pharmaceutically acceptable bases, either inorganic bases, e.g. alkali metal, especially sodium or potassium, or alkaline-earth metal, especially calcium or magnesium hydroxides, or organic bases, e.g. alkylamines, preferably triethylamine, or basic naturally occurring aminoacids, preferably arginine, as well as the internal salts, i.e. zwitterions, are included within the scope of the present invention.

The alkyl and alkylene groups may be branched or straight chain groups.

A $C_1-C_3$ alkyl group is preferably methyl, ethyl or n-propyl.

A $C_1-C_6$ alkyl group is preferably a $C_1-C_4$ alkyl group, in particular methyl, ethyl, n-propyl, isopropyl or isobutyl.

A $C_1-C_3$ alkoxy group is, preferably, methoxy or ethoxy, particularly methoxy.

A $C_2-C_5$ alkylene group is, preferably, ethylene, 1,1'-dimethyl-ethylene or a 1,1' - or 2,2'-dimethyl propylene radical.

A halogen is, preferably, chlorine, bromine or fluorine, in particular chlorine or fluorine.

When the substituent R is other than hydrogen, it is preferably located in position ortho in respect to the carbon atom of the phenyl ring which bears the 1,4-dihydro pyridine substituent. In the group —OR' representing one or both the groups $R_1$ and $R_2$, R' is, preferably, unsubstituted $C_1-C_6$ alkyl, in particular methyl, ethyl or isopropyl.

When one of $R_1$ and $R_2$ is a group

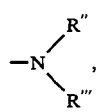

it is, preferably, —NH$_2$.

When one of $R_1$ and $R_2$ is a group —OR$^{IV}$ and R$^{IV}$ is a substituent as defined above under (i), (ii), (iii) or (iv), the group Ph therein preferably represents a phenyl group either unsubstituted or substituted by $C_1-C_3$ alkoxy, in particular methoxy, or halogen, in particular chlorine.

When R$^{IV}$ is a substituent as defined above under (ii) the $C_2-C_5$ alkylene Q radical therein is preferably 1,1'-dimethyl ethylene, 1,1'-dimethyl propylene or 2,2'-dimethyl propylene. A representative example of a group-R$^{IV}$ as defined above under (i) may be the group

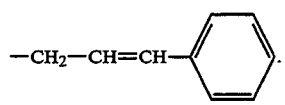

Representative examples of groups R$^{IV}$ as defined above under (ii) may be the following:

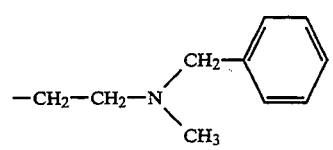

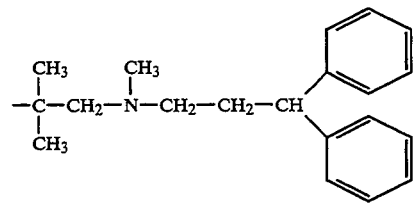

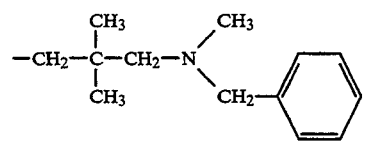

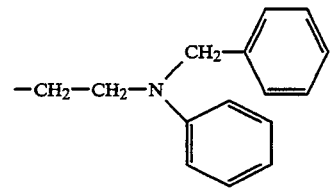

Representative examples of groups R$^{IV}$ as defined above under (iii) are the following:

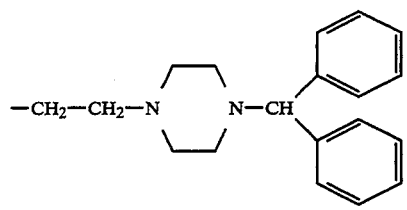

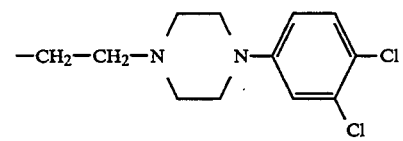

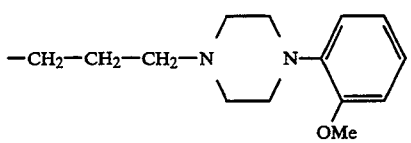

Representative example of a group R$^{IV}$ as defined above under (iv) is:

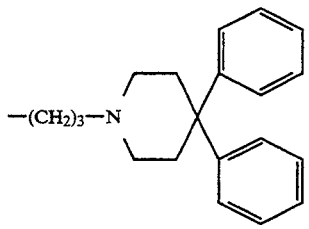

Preferred new compounds having formula (I) are those wherein, subject to the above proviso, Het is as defined above;

A is a direct linkage;

R is hydrogen;

one of $R_1$ and $R_2$ is a group —OR′ wherein R′ is $C_1$–$C_6$ alkyl either unsubstituted or substituted by $C_1$–$C_3$ alkoxy and the other is, independently, a group —OR′ in which R′ is as defined above;

a group —NR″R‴ in which each of R″ and R‴, which may be the same or different, is hydrogen or $C_1$–$C_3$ alkyl; or a 2-[methyl(phenylmethyl)amino]ethoxy group;

$R_3$, $R_4$ and $R_5$ are as defined above, and the pharmaceutically acceptable salts thereof.

Specific examples of preferred compounds of formula (I) according to the present invention are:

1,4-Dihydro-1,2,6-trimethyl-4-[3-(1H-imidazol-1-yl)phenyl]-3,5-pyridinedicarboxylic acid, diethyl ester; (±) 1,4-Dihydro-2-[(2-phthalimidoethoxy)-methyl]-6-methyl-4-[3-(1H-imidazol-1-yl)phenyl]-3,5-pyridinedicarboxylic acid, 3-ethyl 5-methyl ester;

(±) 1,4-Dihydro-2-(methoxy)methyl-6-methyl-4-[3-(1H-imidazol-1-yl)phenyl]-3,5-pyridinedicarboxylic acid, 3-ethyl 5-methyl ester; and (±) 1,4-Dihydro-5-acetyl-2,6-dimethyl-4-[3-(1H-imidazol-1-yl)phenyl]-3-pyridinecarboxylic acid, methyl ester;

1,4-dihydro-1,2,6-trimethyl-4-[4-(1H-imidazol-1-yl)phenyl]-3,5-pyridinedicarboxylic acid, diethyl ester;

1,4-dihydro-1-(N-morpholinoethyl)-2,6-dimethyl-4-[3-(1H-imidazol-1-yl)phenyl]-3,5-pyridinedicarboxylic acid, diethyl ester;

1,4-dihydro-1-(N-morpholinoethyl)-2,6-dimethyl-4-[4-(1H-imidazol-1-yl)phenyl]-3,5-pyridinedicarboxylic acid, diethyl ester;

1,4-dihydro-1,2,6-trimethyl-4-[3-(pyridine-3-yl)phenyl]-3,5-pyridinecarboxylic acid, diethyl ester;

1,4-dihydro-1,2,6-trimethyl-4-[3-(pyridin-3-yl)phenyl]-3,5-pyridinedicarboxylic acid, diisobutyl ester;

1,4-dihydro-1,2,6-trimethyl-4-[4-(pyridin-3-yl)phenyl]-3,5-pyridinedicarboxylic acid, diethyl ester;

1,4-dihydro-1-(N-morpholinoethyl)-2,6-dimethyl-4[3-(pyridin-3-yl)phenyl]-3,5-pyridinedicarboxylic acid, diethyl ester; and the pharmaceutically acceptable salts thereof.

A further object of the present invention are the following compounds and the pharmaceutically acceptable salts thereof, which are new and are encompassed by the chemical general formula disclosed by WO 90/06923, but therein not disclosed as specific chemical entities:

1,4-dihydro-2,6-diethyl-4-[4-(1H-imidazol-1-yl)phenyl]-3,5-pyridinedicarboxylic acid, diethyl ester; 1,4-dihydro-2,6-dimethyl-4-[4-(1H-imidazol-1-yl)phenyl]-3,5-pyridinedicarboxylic acid, dimethyl ester; and 1,4-dihydro-2,6-dimethyl-4-[4-(1H-imidazol-1-yl)phenyl]-3,5-pyridinedicarboxylic acid, ethyl isobutyl ester; and 1,4-dihydro-2,6-dimethyl-4-[4-(1H-imidazol-1-yl)phenyl]-3,5-pyridinedicarboxylic acid, diethyl ester.

The new compounds provided by the present invention, namely the compounds of formula (I) as defined above and the new compounds encompassed by WO 90/06923, and the salts thereof, can be prepared by a process comprising a) reacting a compound of formula (II)

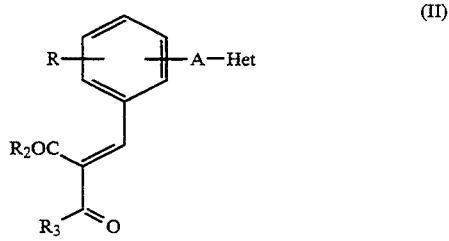

wherein R, A, Het, $R_2$ and $R_3$ are as defined above, with a compound of formula (III)

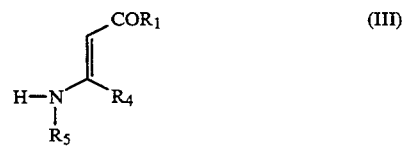

wherein $R_1$, $R_4$ and $R_5$ are as defined above; or b) reacting a compound of formula (II) with a compound of formula (IV)

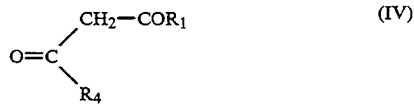

wherein $R_1$ and $R_4$ are as defined above, in the presence of an ammonium salt or hydroxide, thus obtaining a compound of the invention wherein R, A, Het, $R_1$, $R_2$, $R_3$ and $R_4$ are as defined above, and $R_5$ is hydrogen; or c) reacting a compound of formula (V)

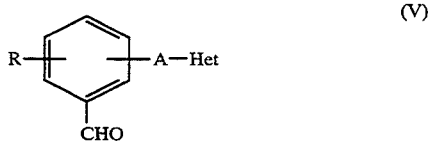

wherein R, A and Het are as defined above, with a compound of formula (III) and a compound of formula (IV) together; or d) reacting a compound of formula (V) with a compound of formula (IV) wherein $R_1$ is a group —OR′ as defined above in the presence of an ammonium salt or hydroxide, thus obtaining a compound of the invention wherein R, A, Het, $R_3$, $R_4$ and $R_5$ are as defined above and each of $R_1$ and $R_2$ is a group —OR' wherein R' is as defined above, and wherein $R_1$ is equal to $R_2$ and $R_3$ is equal to $R_4$; or e) alkylating a compound of the invention wherein $R_5$ is hydrogen to obtain a corresponding compound of the invention in which $R_5$ is $C_1$-$C_6$ alkyl unsubstituted or substituted as defined above; or f) converting a compound of the invention wherein $R_a$ and $R_b$, being as defined above, taken together with the nitrogen atom to which they are linked form a phthalimido group, into another compound of the invention wherein $R_a$ and $R_b$ are hydrogen; and, if desired, converting a compound of the invention into another compound of the invention, and/or, if desired, converting a compound of the invention into a pharmaceutically acceptable salt thereof, and/or, if desired, converting a salt into a free compound, and/or, if desired, separating a mixture of isomers of compounds of the invention, into the single isomers.

The reactions described above under a), b), c) and d) can be performed by using known methods of the organic chemistry and, particularly, those typical of the chemistry of 1,4-dihydro-pyridines, such as those described e.g. by U. Eisner and J. Kuthan in Chem. Rev. 72, 1 (1972) and by D. M. Stout and A. I. Meyers in Chem. rev. 82, 223, (1982).

In particular, reactions such as those described under a), b), c) and d) may be carried out following the same basic procedure, e.g. by heating the reactants at a temperature ranging from about 50° C. to about 150° C. in a suitable inert organic solvent such as, e.g. methanol, ethanol, isopropanol, dioxane, tetrahydrofuran, dimethylformamide, acetonitrile, dimethylsulfoxide, pyridine or their mixtures.

The ammonium hydroxide used in processes b) and d) may be, for example, in the form of concentrated aqueous ammonia, while an ammonium salt may be, for instance, ammonium acetate.

Alkylation of a compound of the invention wherein $R_5$ is hydrogen, according to process variant e), may be carried out by reaction with a suitable optionally substituted $C_1$-$C_6$-alkyl halide, preferably the iodide, in the presence of dry alkaline hydroxide, preferably potassium hydroxide, at room temperature, under an inert gas atmosphere, e.g. nitrogen atmosphere, in an inert solvent e.g. dimethylsulfoxide.

The conversion of a compound of the invention into another compound of the invention, according to process f) above, may be carried out by one of the methods known from the art for removing the phtahlimido group. Preferably the phthalimido derivative is reacted with methylamino solution, in water or in a suitable dialkylether, e.g., diisopropylether, or with aqueous hydrazine solution, preferably at room temperature. Further optional conversions of a compound of the invention into another include, e.g. the following: a compound of the invention containing an esterified carboxy group may be converted in a compound of the invention containing

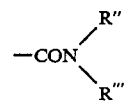

wherein R" and R''' are as defined above, according to known methods.

For example, the conversion of an esterified carboxy group into the corresponding amide may be performed by direct reaction with ammonia or an appropriate amine in a suitable solvent, e.g. ether or benzene or using am excess of the amine as solvent, at temperatures ranging from room temperature to reflux.

Intermediate reactive derivatives may be active esters e.g. $NO_2$-phenyl esters, or N-hydroxysuccinimide esters, acid halides, preferably chloride, mixed anhydrides e.g. ethoxycarbonyl or tert-butylcarbonyl anhydrides, or the reactive intermediates obtained in situ by reaction of the acid with dicyclohexylcarbodiimide or carbonyldiimidazole.

The reactive intermediates, obtained following conventional ways, as those usually employed in the synthesis of peptides, are reacted with ammonia or an appropriate amine in a suitable solvent or with an excess of the amine itself at temperatures ranging preferably from about $-10°$ C. to about 50° C. The optional salification of a compound of the invention as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography, either column chromatography or high pressure liquid chromatography.

Compounds of formula (II) may be prepared by reacting a compound of formula (V) with a compound of formula (IV) following the well known procedure for the Knoevenagel reaction, such as, e.g. described by G. Jones in Org. Reactions, 15 (1967) p. 204–599. Of course the meanings of $R_1$ and, respectively, $R_4$ in the compound (IV) must be those wanted for $R_2$ and, respectively, $R_3$ in the compound (II).

The process is preferably carried out by reacting compounds (IV) and (V) in the presence of a suitable base, e.g. diethylamine or pyridine, in a suitable solvent, e.g. ethanol or benzene, at temperatures ranging approximately from room temperature to the reflux.

Compounds of formula (III) and (IV) are known compounds or may be prepared following usual procedures from known compounds. Compounds of formula (V) are known compounds too or may be prepared by known methods from known compounds e.g. by reducing the corresponding alkyl esters of formula (VI)

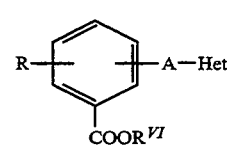

(VI)

wherein

R, A and Her are as defined above and $R^{VI}$ is $C_1$-$C_6$ alkyl.

The reduction may be performed in the presence of a suitable reducing agent as, e.g. diisobutylaluminium hydride in a suitable solvent such as, e.g., diethylether or tetrahydrofuran, at temperatures ranging from about −80° C. to the room temperature. Alternatively, compounds of formula (V) may be prepared by oxidation of the corresponding alcohol of formula (VII)

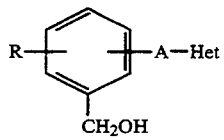

(VII)

wherein

R, A and Het are as defined above.

The process of oxidation may be performed following well known procedures for converting a primary alcohol to the corresponding aldehyde, e.g. those described by J. March in Advanced Organic Chemistry 1985, J. Wiley Publ., p. 1057–1060. Moreover compounds of formula (V), wherein A is a direct linkage, may be prepared by oxidation of compounds of formula (VIII)

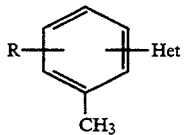

(VIII)

wherein

R and Het are as defined above.

The process of oxidation may be performed following known procedure, e.g. by use of chromic anhydride in acetic anhydride. Compounds of formula VI, VII and VIII are known compounds or may be prepared-following known procedures, e.g. those reported in J. Med. Chem. (1981) 24, 1475 or in J. Med. Chem. (1981), 24, 1149 or in the European Patent Application 17317A2. In particular compounds of formulae (VI) and (VII) wherein Het is the imidazolyl radical

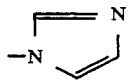

may be prepared, for example, by reacting imidazole or a salt thereof, e.g. sodium salt, with, respectively, compounds of formula (IX) or of formula (X)

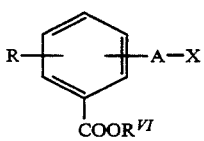

(IX)

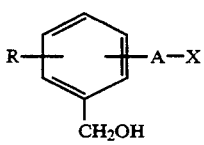

(X)

wherein R, A and $R^{VI}$ are as defined above and X is a suitable leaving group, such as, for example, a suitable halogen, preferably chlorine or bromine, or a tosyl or a mesyl group, following experimental procedures well known from the chemical literature.

Compounds (IX) and (X) are known compounds.

The new compounds of formula (I) and the new chemical entities, encompassed by WO 90/06923, which are a further object of the present invention are capable of promoting the activity of antitumor agents against various kinds of tumor cells, including multiple drug resistant cells, and therefore are useful in cancer chemotherapy in mammals, including humans.

Antitumor promoting activity has also been found for the imidazolyl and pyridyl derivatives previously disclosed by WO 90/0692. The new compounds according to the present invention and the known ones from WO 90/06923 are herein defined as "the compounds of the invention" and are all together represented by formula (IA) as herein defined.

By virtue of their antitumor promoting activity the compounds of the invention can be used in a combined method of treatment with antitumor agents by using combinations of relatively low doses of antitumor agents, thus preventing the serious side-effects of the latter agents in clinical chemotherapy. Accordingly a further object of the present invention is the use of a compound of formula (IA)

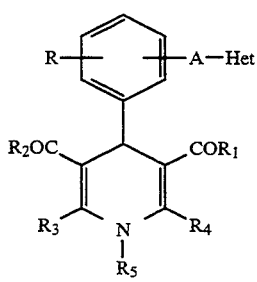

(IA)

wherein Het is

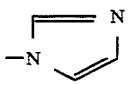

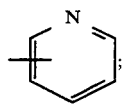

or

A represents a direct linkage, —CH$_2$—, —CH$_2$—CH$_2$— or, when Het is

A may also represent —CH=CH—; R is hydrogen, halogen, $C_1$–$C_3$ alkyl or $C_1$–$C_3$ alkoxy; one of $R_3$ and $R_4$ is $C_1$–$C_3$ alkyl unsubstituted or omega substituted by $C_1$–$C_3$ alkoxy, and the other independently is:

a) $C_1$–$C_3$ alkyl unsubstituted or omega substituted by $C_1$–$C_3$alkoxy; or b)

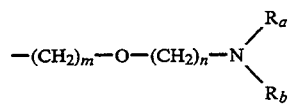

wherein each of m and n which may be the same or different is an integer of 1 to 3, each of $R_a$ and $R_b$ which may be the same or different is hydrogen or $C_1$-$C_3$ alkyl or $R_a$ and $R_b$ taken together with the nitrogen atom to which they are linked from a phthalimido group;

$R_5$ is hydrogen or $C_1$-$C_6$ alkyl unsubstituted or substituted by a —N($R_c$ $R_d$) group in which each of $R_c$ and $R_d$ independently is hydrogen or $C_1$-$C_4$ alkyl, or $R_c$ and $R_d$ taken together with the nitrogen atom to which they are linked form a morpholino or piperidino group;

one of $R_1$ and $R_2$ is a group —OR' wherein R' is $C_1$-$C_6$ alkyl either unsubstituted or omega substituted by cyano or $C_1$-$C_3$-alkoxy and the other is, independently, c) $C_1$-$C_3$ alkyl;
d) a group —OR' as defined hereabove; or
e) a group

wherein each of R" and R'" which may be the same or different, is hydrogen or $C_1$-$C_3$ alkyl; or f) a group —$OR^{IV}$ wherein $R^{IV}$ is hydrogen or a substituent selected from the group consisting of —$(CH_2)_{m'}$—CH=CH—Ph, wherein M' is an integer of 1 to 3 and Ph is a phenyl group either unsubstituted or substituted by one to three substituents chosen among $C_1$-$C_3$ alkyl, $C_1$-$C_3$ alkoxy and halogen;

(ii)

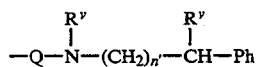

wherein Ph is as defined above; Q is a $C_2$-$C_5$ alkylene radical; n' is zero, 1 or 2; and each $R^V$ is, independently, hydrogen, $C_1$-$C_3$ alkyl or Ph, wherein Ph is as defined above;

(iii)

wherein m, n and Ph are as defined above; and (iv)

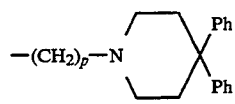

wherein p is 2 or 3 and Ph is as defined above; or a pharmaceutically acceptable salt thereof, in the preparation of a pharmaceutical composition for use in promoting the activity of an antitumor agent.

Specific examples of preferred compounds of formula (IA) are the following 1,4-dihydro-2,6-dimethyl-4-[4-(1H-imidazol-1-yl)phenyl]-3,5-pyridinedicarboxylic acid, diethyl ester;

1,4-dihydro-1,2,6-trimethyl-4-[4-(1H-imidazol-1-yl)phenyl]-3,5-pyridinedicarboxylic acid, diethyl ester;

1,4-dihydro-1-(N-morpholinoethyl)-2,6-dimethyl-4-[3-(1H-imidazol-1-yl)phenyl]-3,5-pyridinedicarboxylicacid, diethyl ester;

1,4-dihydro-1-(N-morpholinoethyl)-2,6-dimethyl-4-[4-(1H-imidazol-1-yl)phenyl]-3,5-pyridinedicarboxylic acid, diethyl ester;

1,4-dihydro-1,2,6-trimethyl-4-[3-(pyridin-3-yl)phenyl]-3,5-pyridinedicarboxylic acid, diethyl ester;

1,4-dihydro-1,2,6-trimethyl-4-[3-(pyridin-3-yl)phenyl]-3,5-pyridinedicarboxylic acid, diisobutyl ester;

1,4-dihydro-1,2,6-trimethyl-4-[4-(pyridin-3-yl)phenyl]-3,5-pyridinedicarboxylic acid, diethyl ester;

1,4-dihydro-1-(N-morpholinoethyl)-2,6-dimethyl-4-[3-(pyridin-3-yl)phenyl]-3,5-pyridinedicarboxylicacid, diethyl ester;

1,4-dihydro-2,6-diethyl-4-[4-(1H-imidazol-1-yl)phenyl]-3,5-pyridinedicarboxylic acid, diethyl ester;

1,4-dihydro-2,6-dimethyl-4-[4-(1H-imidazol-1-yl)phenyl]-3,5-pyridinedicarboxylic acid, dimethyl ester;

1,4-dihydro-2,6-dimethyl-4-[4-(1H-imidazol-1-yl)phenyl]-3,5-pyridinedicarboxylic acid, ethyl isobutyl ester;

1,4-dihydro-1,2,6-trimethyl-4-[3-(1H-imidazol-1-yl)phenyl]-3,5-pyridinedicarboxylic acid, diethyl ester;

(±) 1,4-Dihydro-2-[(2-phthalimidoethoxy)methyl]-6-methyl-4-]3-(1H-imidazol-1-yl )phenyl[-3,5-pyridinedicarboxylic acid, 3-ethyl 5-methyl ester;

(±) 1,4-Dihydro-2-(methoxy)methyl-6-methyl-4-[3-(1H-imidazol-1-yl )phenyl[-3,5-pyridinedicarboxylic acid, 3-ethyl 5-methyl ester;

(±) 1,4-Dihydro-5-acetyl-2,6-dimethyl-4-]3-(1H-imidazol-1-yl)phenyl]-3-pyridinecarboxylic acid, methyl ester;

1,4-Dihydro-2,6-dimethyl-4-[3-(1H-imidazol-1-yl)phenyl]-3,5-pyridinedicarboxylic acid, diethyl ester, m.p. 202°–204° C.;

1,4-Dihydro-2,6-dimethyl-4-[3-(1H-imidazol-1-yl-methyl)phenyl]-3,5-pyridinedicarboxylic acid, diethyl ester, m.p. 196°–199° C.;

1,4-Dihydro-2,6-dimethyl-4-[3-(1H-imidazol-1-yl)phenyl]-3,5-pyridinedicarboxylic acid, dimethyl ester, m.p. 212°–216° C.;

1,4-Dihydro-2,6-dimethyl-4-[2-(1H-imidazol-1-yl)phenyl]-3,5-pyridinedicarboxylic acid, diethyl ester, m.p. 208°–210° C.;

1,4-Dihydro-2,6-diethyl-4-[3-(1H-imidazol-1-yl)phenyl]-3,5-pyridinedicarboxylic acid, diethyl ester, m.p. 171°–172° C.;

1,4-Dihydro-2,6-dimethyl-4-[2-(1H-imidazol-1-yl)phenyl-]-3,5-pyridinedicarboxylic acid, diethyl ester, m.p. 208°–210° C.;

1,4-Dihydro-2,6-diethyl-4-[3-(1H-imidazol-1-yl)phenyl]-3,5-pyridinedicarboxylic acid, diethyl ester, m.p. 171°-172° C.;

1,4-Dihydro-2,6-dimethyl-4-[3-(1H-imidazol-1-yl)phenyl-]-3,5-pyridinedicarboxylic acid, ethyl methyl ester, m.p. 197°-200° C.;

1,4-Dihydro-2,6-dimethyl-4-[3-1H-imidazol-1-yl)phenyl]-3,5-pyridinedicarboxylic acid, 2-cyanoethyl ethyl ester, Elemental analysis: Found: C 65.38; H 5.73; N 13.15 Calculated for $C_{23}H_{24}N_4O_4$: C 65.70; H 5.75; N 13.32 N.M.R. (DMSO-$a_6$) δ p.p.m.: 1.10 (3H, t,$CH_2CH_3$) 2.28 (6H,s,=C—$CH_3$) 2.58 (2H,t,$COOCH_2CH_2C\underline{N}$) 4.01 (2H,q,$C\underline{H}_2CH_3$) 4.05 (2H,t,$COOC\underline{H}_2CH_2CN$) 4.93 (1H,s,$C\underline{H}$ at 4 position of dihydropyridine) 7.05-7.6 (6H,m,phenylic+CH=CH imidazolic protons) 8.09 (1H,dd,N—$C\underline{H}$—N) 8.88 (1H,s,NH);

1,4-Dihydro-2,6-dimethyl-4-[3-(1H-imidazol-1-yl)phenyl-]-3, 5-pyridinedicarboxylic acid, ethyl 2-[methyl (phenylmethyl) amino]ethyl ester, Elemental analysis: Calculated for: $C_{30}H_{34}N_4O_4$: C 70.02; H 6.66; N 10.89 Found: C 69.17; H 6.72; N 10.72 T.L.C.: eluant $CHCl_3/CH_3OH=95/5$, $R_f=0.34$ N.M.R. ($CDCl_3$) δ p.p.m.: 1.22 (3H,t,$CO_2CH_2CH_3$) 2.20 (3H,s,N($CH_3$)($CH_2Ph$)) 2.37 (6H,s,2=C—$C\underline{H}_3$) 2.69 (2$\underline{H}$,t,$C\underline{H}_2$N($CH_3$)($CH_2Ph$)) 3.50 (2H,s,N($CH_3$)($C\underline{H}_2Ph$)) 4.11 (2H,q,$CO_2C\underline{H}_2CH_3$) 4.21 (2H,t,$CO_2C\underline{H}_2CH_2$—) 5.11 (1H,s,$C\underline{H}$ at 4 position of dihydropyridine) 5.89 (1H,s,$N\underline{H}$) 7.10-7.40 (11H,m,$C\underline{H}$ at 2,4,5,6 positions of phenyl ring, $C\underline{H}$ at 4,5 positions of imidazole and phenyl hydrogens of ester function) 7.78 (1H,dd,$C\underline{H}$ at 2 position of imidazole) MS: m/z 514 M+;

1,4-Dihydro-2,6-dimethyl-4-[3-(1H-imidazol-1 -yl)-phenyl-]3, 5-pyridinedicarboxylic acid, ethyl ester (monohydrate), m.p. 117°-121° C. dec.

1,4-Dihydro-2,6-dimethyl-4-[3-(3-pyridyl)phenyl]-3,5-pyridinedicarboxylic acid, diethyl ester, m.p. 183°-6° C.

1,4-Dihydro-2,6-dimethyl-4-[3-(3-pyridyl)phenyl]-3,5-pyridinedicarboxylic acid, diisobutyl ester, m.p. 97°-8° C.

1,4-Dihydro-2,6-dimethyl-4-[3-(3-pyridyl)phenyl]-3,5-pyridinedicarboxylic acid, ethyl 2-[methyl(-phenylmethyl) amino]ethyl ester, as an oil.

Elemental analysis: Found: C 71.90; H 6.85; N 7.75 Calculated for $C_{32}H_{35}N_3O_4$: C 73.12; H 6.71; N 7.99 TLC: eluant $CHCl_3/CH_3OH=95/5$ RF=0.5 NMR ($CDCL_3$) δ p.p.m.: 1.21 (3H,t,$CH_2CH_3$) 2.16 (3H,s,N($CH_3$)($CH_2Ph$)) 2.35 (6H,s, =C—$C\underline{H}_3$) 2.64 (2H,t,$C\underline{H}_2N(CH_3)(CH_2Ph)$) 3.45 (2H,s,N($CH_3$)($C\underline{H}_2Ph$)) 4.12 (2H,q,$COOCH_2CH_3$)

and the pharmaceutically acceptable salts thereof.

A further object of the present invention is a combined method of treatment of cancer in mammals, including humans, in need of such treatment, said method comprising administering
1) a compound of formula (IA), or a pharmaceutically acceptable salt thereof, and
2an antitumor agent, in amounts and close enough together in time sufficient to effect a therapeutically useful interaction. Object of the present invention is also to provide products containing a compound of formula (IA), or a pharmaceutically acceptable salt, and an antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Antitumor agents that can be formulated with a compound of the invention or alternatively, can be administered in a combined method of treatment are e.g. doxorubicin, daunomycin, epirubicin, idarubicin, etoposide, fluorouracil, mephalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent. A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The antitumor promoting activity of the compounds of the invention is proven for example by the fact that they are able to reduce the resistance to doxorubicin, as herebelow reported.

MATERIALS AND METHODS

Cells and Culture Conditions

LoVo and LoVo/DX cells (human colon adenocarcinoma cell lines sensitive and resistant to Doxorubicin, respectively) were maintained at 37° C. in a humidified atmosphere of 5% $CO_2$. Culture medium was Ham's F12 supplemented with 10% foetal calf serum, 1% vitamins (BME vitamin solution 100 X), and 1% glutamine (200 mM). Both cell lines were passaged twice weekly.

Drugs

Doxorubicin, from Farmitalia Carlo erba, was dissolved in sterile water, and the concentrations were checked spectro-photometrically. Solutions of the compounds of the invention using ethanol were prepared immediately before use. Ethanol at the maximal final concentration used (1%) had not any detectable effect on cell proliferation.

Cytotoxic Evaluation

A single-cell plating technique was utilized for measuring the colony-inhibiting efficacy of drugs alone or drug combinations.

Exponentially growing LoVo and LoVo/DX cells were adjusted to the concentration of 300 cells.$ml^{-1}$ and seeded in 36mm Petri dishes (2 ml/dish).

After 48h incubation, medium was withdrawn and solutions of invention compounds alone, or Doxorubicin alone or solutions of the combination of both compounds, were added. Exposure to drugs was for 4h, cells were then washed with saline and fresh growth medium added, subsequently, dishes were incubated for 7 days.

Survival was determined as the percentage of colonies in treated samples vs untreated ones. For combination of the compounds of the invention and doxorubicin, survival was calculated using as controls the number of colonies in samples treated with compounds of the invention alone.

RESULTS

The compounds of the invention have been tested on LoVo and LoVo/DX cells as described in materials and methods. Table 1 shows the effects of representative compounds of the invention on the cytotoxicity of Doxorubicin on LoVo/DX cells in comparison with Nifedipine (GB-1,173,862) which has a closely related chemical structure.

The compounds were used at the maximal concentrations which, when given alone, had no cytotoxic effects either on LoVo and LoVo/DX cells. All the compounds of the invention, when tested in combination with Doxorubicin, increase the citotoxicity of the latter only on LoVo/DX cells, reducing the Resistance Index from 49.1 (Doxorubicin alone) to <3.2 (compounds plus Doxorubicin). On LoVo cells the cytotoxic activity of Doxorubicin alone or in combination with the tested compounds remains unchanged (IC50≈100 ng/ml).

TABLE 1

Effect of representative derivatives of the invention on Doxorubicin cytotoxicity on LoVo/DX cells.

| Compounds | IC50* | R.I.** |
| --- | --- | --- |
| Doxorubicin | 4913 | 49.1 |
| Doxorubicin + FCE 24265 (20 μg/ml) | 320 | 3.2 |
| Doxorubicin + FCE 26341 (20 μg/ml) | 210 | 2.1 |
| Doxorubicin + FCE 26262 (20 μg/ml) | 200 | 2.0 |
| Doxorubicin + FCE 26224 (10 μg/ml) | 200 | 2.0 |
| Doxorubicin + FCE 27335 (20 μg/ml) | 195 | 1.9 |
| Doxorubicin + FCE 26332 (20 μg/ml) | 144 | 1.4 |
| Doxorubicin + Nifedipine (10 μg/ml) | 4350 | 43.5 |

*IC50 = Concentration inhibiting 50% of colony formation

**R.I. = Resistance Index = $\frac{IC50 \text{ LoVo/DX}}{IC50 \text{ LoVo}}$

The IC50 of LoVo cells was =100 ng/ml.

FCE 24265 is: 1,4-dihydro-2,6-dimethyl-4-[3-(1H-imidazol-1-yl)phenyl]-3,5-pyridinedicarboxylic acid, diethyl ester;

FCE 26341 is: (±)-1,4-dihydro-2-methoxymethyl-6-methyl-4-[3-(1H-imidazol-1-yl)phenyl]-3,5-pyridinedicarboxylic acid, 3-ethyl-5-methyl ester;

FCE 26262 is: 1,4-dihydro-1,2,6-trimethyl-4-[3-(1H-imidazol-1-yl)phenyl]-3,5-pyridinedicarboxylic acid, diethyl ester;

FCE 26224 is: 1,4-dihydro-2,6-dimethyl-4-[3-(pyridin-3-yl)phenyl]-3,5-pyridinedicarboxylic acid, diisobutyl ester;

FCE 27335 is: 1,4-dihydro-2,6-dimethyl-4-[4-(1H-imidazol-1-yl)phenyl]-3,5-pyridinedicarboxylic acid, diethyl ester;

FCE 26332 is: 1,4-dihydro-2-[(2-phthalimidoethoxy)-methyl]-6-methyl-4-[3-(1H-imidazol-1-yl)phenyl]-3,5-pyridinedicarboxylic acid, 3-ethyl 5-methyl ester.

The toxicity of the compounds of the invention is negligible, so that they can be safely used in therapy.

Mice which had been deprived of food for nine hours were treated orally with single administrations of increasing doses of compounds of the invention, then housed and normally fed. For example the orientative acute toxicity ($LD_{50}$) of the compound FCE 24265, assessed on the seventh day after treatment, was higher than 800 mg/kg. In view of their low toxicity the compounds of the invention can be safely used in medicine.

The therapeutic regimen for the different clinical syndromes must be adapted to the type of pathology taking into account, as usual, also the route of administration, the form in which the compound is administered and the age, weight and conditions of the subject involved.

The dosage level suitable for oral administration to adult humans of the compounds of the invention, e.g. of 1,4-dihydro-2,6-dimethyl-4-[3-(1H-imidazol-1-yl)phenyl]-3,5-pyridinedicarboxylic acid, diethyl ester and 1,4-dihydro-2,6-dimethyl-4-[3-(3-pyridyl)phenyl]-3,5-pyridinedicarboxylic acid, diethyl ester may range from about 5 mg to about 500 mg per dose 1 to 3 times a day, preferably from about 20 mg to about 150 mg per dose 1 to 3 times a day. Of course, these dosage regimens may be adjusted to provide the optimal therapeutic response.

As already said, the present invention includes ion its scope also the pharmaceutical compositions containing the compounds of formula (I) in association with pharmaceutically acceptable carriers or diluents.

A further object of this invention is to provide a pharmaceutical composition comprising a suitable carrier and/or diluent and, as an active principle, a compound selected from 1,4-dihydro-2,6-diethyl-4-[4-(1H-imidazol-1-yl)phenyl]-3,5-pyridinedicarboxylic acid, diethyl ester;

1,4-dihydro-2,6-dimethyl-4-[4-(1H-imidazol-1-yl)phenyl]-3,5-pyridinedicarboxylic acid, dimethyl ester;

1,4-dihydro-2,6-dimethyl-4-[4-(1H-imidazol-1-yl)phenyl]-3,5-pyridinedicarboxylic acid, ethyl isobutyl ester; and 1,4-dihydro-2,6-dimethyl-4-[4-(1H-imidazol-1-yl)phenyl]-3,5-pyridinedicarboxylic acid, diethyl ester, or a pharmaceutically acceptable salt thereof.

The nature of the pharmaceutical composition will, of course, depend upon the desired route of administration.

The compositions may be formulated in the conventional manner with the usual ingredients. For example, the compounds of the invention may be administered in the form of aqueous or oily solutions or suspensions, tablets, pills, capsules, syrups, drops or suppositories.

Thus, for oral administration, the pharmaceutical compositions containing the compounds of this invention are preferably sugar or film coated tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as staches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations.

Said pharmaceutical preparations may be manufactured in known manner, for example by means of mixing, granulating, tabletting, sugar-coating, or film-coating processes.

The liquid dispersions for oral administration may be, e.g., syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as a carrier, for example, sterile water or, preferably, they may be in the form of sterile aqueous isotonic saline solutions. The suppositories may contain, together with the active compound, a pharmaceutically acceptable carrier e.g. cocoa-butter, polyethylene glycol, a polyoxyethylene sorbitan fatty acid ester surfactant or lecithin.

In this specification the abbreviations "OMe", "OEt", "OiPr", "Et$_2$O", "AcOH" stand, respectively, for "methoxy", "ethoxy", "isopropoxy", "diethyl ether", "acetic acid". The following examples illustrate but do not limit the present invention.

EXAMPLE 1

A mixture of 0.910 g (5.29 mmol) of 3-(1H-imidazol-1-yl)benzaldehyde, 1.69 g (5.29 mmol) of ethyl 4-(2-phthalimidoethoxy)acetoacetate and 0.628 g (5.29 mmol) of methyl 3-aminocrotonate in 30 ml of diisopropyl alcohol is refluxed for 12 hours. The reaction mixture is concentrated, diluted with water and extracted with ethyl acetate. The organic layers are put together, dried over an. Na$_2$SO$_4$ and evaporated under vacuum. The oily residue is purified over flash silica-gel column (chloroform/methanol 98/2), yielding 2 g (66%) of yellow oil.

After crystallization from methanol, 1 g of pale yellow solid is obtained, corresponding to (±) 1,4-dihydro-2-[(2-phthalimldoethoxy) methyl]-6-methyl-4-[3-(1H-imidazol-1-yl)phenyl]-3,5-pyridinedicarboxylic acid, 3-ethyl 5-methyl ester. m.p.: 168°–172° C.

Elemental analysis: Found: C 64.87; H 5.31; N 9.93
Calculated for C$_{31}$H$_{30}$N$_4$O$_7$: C 65.25; H 5.30; N 9.82
TLC: eluant chloroform/methanol =97/3 RF=0.4
$^1$H-NMR (DMSO d-$_6$) δ p.p.m.: 1.09 (3H, t, COOCH$_2$CH$_3$) 2.23 (3H, s, =C—CH$_3$) 3.54 (3H, s, COOCH$_3$) 3.60–3.85 (4H, m, —OCH$_2$CH$_2$N=) 3.95 (2H, m, COOCH$_2$CH$_3$) 4.50–4.67 (2H, 2 d, =C—OCH$_2$—) 4.89 (1H, s, CH at 4 position of dihydropyridine) 7.0–8.1 (11H, m, phenyl rings+imidazole ring) 8.40 (1H, s, NH) MS: m/z 570 (6, M+·); 539 (2); 441 (7); 427 (100); 379 (4); 208 (41); 174 (57); 144 (11).

By proceeding analogously the following compounds can be obtained:

(±) 1,4-dihydro-2-(methoxy)methyl-6-methyl-4-[3-(1H-imidazol-1-yl)phenyl]-3,5-pyridinedicarboxylic acid, 3-ethyl 5-methyl ester m.p.: 153°–4° C.

Elemental analysis: Found: C 63.75; H 6.03; N 10.00
Calculated for C$_{22}$H$_{25}$N$_3$O$_5$: C 64.22; H 6.12; N 10.21
TLC: eluant chloroform/menthanol=98/2 RF=0.30
$^1$H-NMR (CDCl$_3$) δ p.p.m.: 1.21 (3H, t, COOCH$_2$CH$_3$) 2.38 (3H, s, =C—CH$_3$) 3.47 (3H, s, —CH$_2$OCH$_3$) 3.65 (3H, s, COOOCH$_3$) 4.1 (2H, m, —COOCH$_2$CH$_3$) 4.58,4.70 (2H, 2d, —CHOCH$_3$) 5.05 (1H, s, CH at 4 position of dihydropyridine) 7.08 (1H, bs, NH) 7.1–7.35 (6H, m, phenyl ring+CH at 4 and 5 positions of imidazole) 7.79 (1H, s, —N=CH—N=) MS: m/z 411 (10, M+); 366 (4); 282 (5); 268 (100); 222 (15); 208 (51); 144 (24).

(±) 1,4-dihydro-5-acetyl-2,6-dimethyl-4-[3-(1H-imidazol-1-yl)phenyl]-3-pyridinecarboxylic acid, methyl ester m.p.: 226° C.

Elemental analysis: Found: C 67.76; H 6.04; N 11.74
Calculated for C$_{20}$H$_{21}$N$_3$O$_3$: C 68.36; H 6.02; N 11.96
TLC: eluant chloroform/methanol=96/4 RF=0.30
$^1$H-NMR (CDCl$_3$) δ p.p.m.: 2.19, 2.31 2.37, (9H, 3 s, COCH$_3$ +$^2$=C—CH$^3$) 3.72 (3H, s, COOCH$^3$) 5.11 (1H, s, CH at 4 position of dihydropyridine) 6.15 (1H, bs, NH) 7.1–7.4 (6H, m, phenyl ring+CH at 4 and 5 positions of imidazole) 7.79 (1H, bs, —N=CH—N=).

EXAMPLE 2

1,4-dihydro-1,2,6-trimethyl-4-[3-(1H-imidazol-1-yl)phenyl]3,5-pyridinedicarboxylic acid, diethyl ester To 0.144 g (0.0026 moles) of finely powdered potassium hydroxide in 15 ml of DMSO, 0.26 g (0.00066 moles) of 1,4-dihydro-2,6-dimethyl-4-[3-(1H-imidazol-1-yl)phenyl]-3,5-pyridinedicarboxylic acid, diethyl ester, are added and stirred for 2 hours at room temperature under a nitrogen atmosphere. Then to the mixture 0.187 g (0.00131 moles) of methyl iodide are added. After 2 hours of stirring, the reaction mixture is poured into water and extracted with ethyl acetate; the organic layer is dried over an. Na$_2$SO$_4$ and evaporated under vacuum. The residue is purified over flash silica-gel column (eluant chloroform/methanol from 1% to 2%), yielding 0.13 g (48%) of pure product.

Elemental analysis: Found: C 66.10; H 6.62; N 9.83
Calculated for C$_{23}$H$_{27}$N$_3$O$_4$: C 67.46; H 6.65; N 10.24
TLC: eluant chloroform/methanol=95/5 RF=0.35
$^1$H-NMR (CDCl$_3$) δ p.p.m.: 1.27 (6H, t, 2 COOCH$_2$CH$_3$) 2.49 (6H, s, 2 =C—CH$_3$) 3.21 (3H, s, =N—CH$_3$) 4.19 (4H, q, 2 COOCH$_2$CH$_3$) 5.12 (1H, s, CH at 4 position of dihydropyridine) 7.0–7.3 (6H, m, phenyl ring+CH at 4 and 5 positions of imidazole ) 7.78 (1H, bs, —N=CH—N—).

By proceeding analogously the following compounds can be obtained:

1,4-dihydro-1,2,6-trimethyl-4-[4-(1H-imidazol-1-yl)phenyl]-3,5-pyridinedicarboxylic acid, diethyl ester, m.p. 80°–83° C.;

1,4-dihydro-1-(N-morpholinoethyl)-2,6-dimethyl-4-[3-(1H-imidazol-1-yl)phenyl]-3,5-pyridinedicarboxylic acid, diethyl ester, m.p. 110°–112° C.;

1,4-dihydro-1-N-morpholinoethyl)-2,6-dimethyl-4-[4-1H-imidazol-1-yl)phenyl]-3,5-pyridinedicarboxylicacid, diethyl ester;

1,4-dihydro-1,2,6-trimethyl-4-[3-(pyridin-3-yl)phenyl]-3,5-pyridinedicarboxylic acid, diethyl ester;

1,4-dihydro-1,2,6-trimethyl-4-[3-(pyridin-3-yl)phenyl]-3,5-pyridinedicarboxylic acid, diisobutyl ester;

1,4-dihydro-1,2,6-trimethyl-4-[4-(pyridin-3-yl)phenyl]-3,5-pyridinedicarboxylic acid, diethyl ester; and 1,4-dihydro-1-(N-morpholinoethyl)-2,6-dimethyl-4-[3-pyridin-3-yl)phenyl]-3,5-pyridinedicarboxylic acid, diethyl ester.

EXAMPLE 3

(±)1,4-dihydro-2-[(2-aminoethoxy)methyl]-4-[3-(1H-imidazol-1-yl)phenyl]-6-methyl-3,5-pyridinedicarboxylic acid, 3-ethyl 5-methyl ester A mixture of 0.8 g (0.0014 moles) of (±) 1,4 dihydro-2-[(2phthalimidoethoxy )methyl]-6-methyl-]4-[3-(1H-imidazol-1-yl) phenyl]-3,5-pyridinedicarboxylic acid, 3-ethyl 5-methyl ester, 9 ml of 20% methylamine diisopropyl ether solution and 10 ml of absolute ethanol is stirred for 2 days at room temperature. The reaction mixture is evaporated to dryness, the residue taken up with ethyl acetate and diethyl ether, and the precipitated solid filtered off. The organic solution is evaporated under vacuum and the residue is purified over flash silica-gel column (eluant: chloroform/methanol/ammonium hydroxide=90/10/0.2), yielding 0.4 g (65%) of an oily product, which is transformed in its maleate salt.

Elemental analysis: Found: C 57.32; H 5.72; N 9.61 Calculated for $C_{27}H_{32}N_4O_9$: C 58.27; H 5.79; N 10.07 TLC: eluant chloroform/methanol/ammonium hydroxide=90/10/0.2 RF=01.8 $^1$H-NMR (DMSO) δ p.p.m.: 1.13 (3H, t, COOCH$_2$CH$_3$) 2.35 (3H, s, =C—CH$_3$) 3.05 (2H, m, CH$_2$NH$_3$+) 3.56 (3H, s, COOCH$_3$) 3.64 (2H, m, OCHH$_2$CH$_2$NH$_3$+) 4.05 (2H, m, COOCH$_2$CH$_3$) 4.50,4.74 (2H, 2d, =C—CH$_2$O) 4.96 (1H, s, CH at 4 position of dihydropyridine) 6.03 (2H, s, HOOCCH=CHCOOH) 7.1–8.2 (7H, m, phenyl ring-+imidazole ring) 7.80 (3H, bs, NH$_3$+) 8.47 (1H, s, NH) MS: m/z 440 (13, M+·); 423 (67); 367 (41); 350 (68); 297 (100); 280 (65); 208 (44); 144 (44).

EXAMPLE 4

A mixture of 17.2 g (0.1 mol) of 4-(1H-imidazol-1-yl)benzaldehyde, 26 g (0.2 mol) of ethyl acetoacetate and 5 ml of concentrated NH$_4$OH in absolute ethanol (25 ml) was refluxed for 6 hours. The mixture was poured into 500 ml of ice-water and the aqueous solution was extracted with methylene chloride. The organic layers were put together, dried over CaCl$_2$ and evaporated under vacuum. The crude product was recrystallized from Et$_2$O, giving 25.7 g (65%) of 1,4-dihydro-2,6-dimethyl-4-[4-(1H-imidazol-1-yl)phenyl]-3,5-pyridinedicarboxylic acid, diethyl ester, m.p. 231°–233° C.

By proceeding analogously the following compounds can be obtained:

1,4-dihydro-2,6-diethyl-4-[4-(1H-imidazol-1-yl)phenyl]-3,5-pyridinedicarboxylic acid, diethyl ester;

1,4-dihydro-2,6-dimethyl-4-[4-(1H-imidazol-1-yl)phenyl]-3,5-pyridinedicarboxylic acid, dimethyl ester; and 1,4-dihydro-2,6-dimethyl-4-[4-(1H-imidazol-1-yl)phenyl]-3,5-pyridinedicarboxylic acid, ethyl isobutyl ester.

EXAMPLE 5

Tablets, each eighing 150 mg and containing 50 mg of the active substance are manufactured as follows:

| Composition (for 10,000 tablets) | |
|---|---|
| 1,4-dihydro-2,6-dimethyl-4-[3-(1H-imidazol-1-yl)phenyl]--3,5-pyridinedicarboxylic acid, diethyl ester | 500 g |
| Lactose | 710 g |
| Corn starch | 237.5 g |
| Talc powder | 37.5 g |
| Magnesium stearate | 15 g |

1,4-dihydro-2,6-dimethyl-4-[3-(1H-imidazol-1-yl]-3,5-pyridinedicarboxylic acid, diethyl ester, lactose and a half of the corn starch are mixed; the mixture is then forced through a sieve of 0.5 mm openings. Corn starch (18 g) is suspended in warm water (180 ml).

The resulting paste is used to granulate the powder. The granules are dried, comminuted on a sieve of sieve size 1.4 mm, then the remaining quantity of starch, talc and magnesium is added, carefully mixed, and processed into tablets using punches of 8 mm diameter.

EXAMPLE 6

Tablets, each weighing 150 mg and containing 50 mg of the active substance are manufactured as follows:

| Composition (for 10,000 tablets) | |
|---|---|
| 1,4-dihydro-2,6-dimethyl-4-(3(3-pyridyl)phenyl)-3,5-pyridinedicarboxylic acid, diethyl ester | 500 g |
| Lactose | 710 g |
| Corn starch | 237.5 g |
| Talc powder | 7.5 g |
| Magnesium stearate | 15 g |

1,4-dihydro-2,6-dimethyl-4-(3(3-pyridyl)phenyl )-3,5-pyridine dicarboxylic acid, diethyl ester, lactose and a half of the corn starch are mixed; the mixture is then forced through a sieve of 0.5 mm openings. Corn starch (18 g) is suspended in warm water (180 ml).

The resulting paste is used to granulate the powder. The granules are dried, comminuted on a sieve of sieve size 1.4 mm, then the remaining quantity of starch, talc and magnesium is added, carefully mixed, and processed into tablets using punches of 8 mm diameter.

We claim:

1. A compound of formula (I)

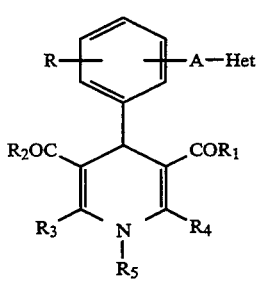

(I)

wherein Het is

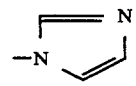

A represents a direct linkage at the phenyl 4-position; R is hydrogen; one of $R_3$ and $R_4$ is $C_1$–$C_3$ alkyl unsubstituted or omega substituted by $C_1$–$C_3$ alkoxy, and the other, independently, is:

a) $C_1$–$C_3$ alkyl unsubstituted or omega substituted by $C_1$–$C_3$ alkoxy; or b) —$(CH_2)_m$—O—$(CH_2)_n$—$NR_aR_b$ wherein each of m and n, which may be the same or different is an integer of 1 to 3, each of $R_a$ and $R_b$, which may be the same or different, is hydrogen or $C_1$-$C_3$ alkyl; $R_5$ is hydrogen or $C_1$-$C_6$ alkyl unsubstituted or substituted by a morpholino;

each of $R_1$ and $R_2$ is independently a group —OR' wherein R' is $C_1$-$C_6$ alkyl; or a pharmaceutically acceptable salt thereof.

2. A compound selected from the group consisting of
1,4-dihydro-2,6-diethyl-4-[4-(1H-imidazol-1-yl)phenyl]-3,5-pyridinedicarboxylic acid, diethyl ester;
1,4-dihydro-2,6-dimethyl-4-[4-(1H-imidazol-1-yl)phenyl]-3,5-pyridinedicarboxylic acid, dimethyl ester;
1,4-dihydro-2,6dimethyl-4-[4-(1H-imidazol-1-yl)phenyl]-3,5-pyridinedicarboxylic acid, ethyl isobutyl ester; and
1,4-dihydro-2,6-dimethyl-4-[4-(1H-imidazol-1-yl)phenyl]-3,5-pyridinedicarboxylic acid, diethyl ester, or a pharmaceutically acceptable salt thereof.

3. A compound selected from the group consisting of 1,4-dihydro-1,2,6-trimethyl-4[4-(1H-imidazol-1-yl)phenyl]-3,5-pyridinedicarboxylic acid, diethyl ester; 1,4-dihydro-1-(N-morpholinoethyl)-2,6-dimethyl-4-[4-(1H-imidazol-1-yl)phenyl]-3,5-pyridinedicarboxylic acid, diethyl ester and pharmaceutically acceptable salts thereof.

4. A pharmaceutical composition containing a compound of formula (I), according to claim 1, or a pharmaceutically acceptable salt thereof, as an active principle, and a pharmaceutically acceptable carrier and/or diluent.

5. A pharmaceutical composition containing a pharmaceutically acceptable carrier and/or diluent and as an active principle a compound selected from
1,4-dihydro-2,6-diethyl-4-[4-(1H-imidazol-1-yl)phenyl]-3,5-pyridinedicarboxylic acid, diethyl ester; 1,4-dihydro-2,6-dimethyl-4-[4-(1H-imidazol-1-yl)phenyl]-3,5-pyridinedicarboxylic acid, diethyl ester;
1,4-dihydro-2,6-dimethyl-4-[4-(1H-imidazol-1-yl)phenyl]-3,5-pyridinedicarboxylic acid, dimethyl ester; and 1,4-dihydro-2,6-dimethyl-4-[4-(1H-imidazol-1-yl)phenyl]-3,5-pyridinedicarboxylic acid, ethyl isobutyl ester; or a pharmaceutically acceptable salt thereof.

* * * * *